US005967969A

United States Patent [19]

Enomoto et al.

[11] Patent Number: 5,967,969

[45] Date of Patent: Oct. 19, 1999

[54] ENDOSCOPIC APPARATUS HAVING A PERIPHERAL LIGHT SOURCE

[75] Inventors: Takayuki Enomoto; Masaaki Nakasima; Tadashi Takahashi, all of Tokyo, Japan

[73] Assignee: Asahi Kogaku Kogyo Kabushiki Kaisha, Tokyo, Japan

[21] Appl. No.: 09/133,578

[22] Filed: Aug. 13, 1998

Related U.S. Application Data

[62] Division of application No. 08/760,396, Dec. 4, 1996, Pat. No. 5,830,121, which is a continuation of application No. 08/330,258, Oct. 27, 1994, abandoned.

[30] Foreign Application Priority Data

| | | | |
|---|---|---|---|
| Oct. 27, 1993 | [JP] | Japan | 5-268472 |
| Nov. 5, 1993 | [JP] | Japan | 5-276313 |
| Jul. 20, 1994 | [JP] | Japan | 6-167755 |
| Jul. 20, 1994 | [JP] | Japan | 6-167756 |

[51] Int. Cl.[6] ........ A61B 1/00

[52] U.S. Cl. ........ 600/117; 600/178; 600/118

[58] Field of Search ........ 600/117, 118, 600/131, 133; 128/908; 348/72

[56] References Cited

U.S. PATENT DOCUMENTS

| | | | |
|---|---|---|---|
| 4,862,258 | 8/1989 | Kidawara et al. | 600/109 |
| 4,862,872 | 9/1989 | Yabe et al. | 600/133 |
| 4,979,497 | 12/1990 | Matsura et al. | 600/131 |
| 4,996,975 | 3/1991 | Nakamura | 600/118 |
| 5,359,993 | 11/1994 | Slater et al. | 600/117 |
| 5,400,267 | 3/1995 | Denen et al. | 128/908 |

*Primary Examiner*—John P. Leubecker

*Attorney, Agent, or Firm*—Kane, Dalsimer, Sullivan, Kurucz, Levy, Eisele and Richard, LLP

[57] ABSTRACT

An endoscope apparatus includes at least one endoscope, a peripheral device having a light source, and a detachable connecting device to connect the endoscope to the peripheral device. The emission time or illumination duration of the light source is measured and stored in the peripheral device. An indicating device is used to display the stored emission time or illumination duration independent of the connection between the endoscope and the peripheral device.

3 Claims, 22 Drawing Sheets

MONITOR
50
VIDEO PROCESSOR AND LIGHT SOURCE DEVICE ( ESSENTIALS SUPPORT DEVICE )
20
21
VIDEO SIGNAL PROCESSOR
IMAGE DATA
22
LIGHT SOURCE
30
MICROCOMPUTER (INTEGRATION MEANS)
45
19
STORAGE CELL FOR TOTAL USAGE OPERATING TIME OR NUMBER OF TIMES CONNECTED
15
17
16
11
13
11a
12
10
14

MONITOR
IMAGE DATA
CRTC
VIDEO RAM
I/O
ROM
RAM
CPU
PIT
PIC
RTC
LAMP CONTROL CIRCUIT
KEYBOARD
PANEL SWITCH
BUZZER
ENDOSCOPE
Vcc

| Serial Number of Endoscope | Total Usage of Operating Time |
|---|---|
| 1020018U | 0h35m |
| 2000047C | 1h02m |
| :<br>: | :<br>: |
| 0320065D | 0h54m |
| :<br>: | :<br>: |
| | |
| | |

E
S73
Disconected
NO
YES
F
S77
u5=0
NO
YES
S78
Lamp On
NO
YES
S74
Calculate Operating Time
S75
Write Operating Time in Address Corresponding to Serial Number of Endoscope Used
S76
u1=0
u5=0
u5=1
S79
Store Present Time
S80
Return

| Serial Number of Endoscope | Last Operating Time | Total Usage of Operating Time |
|---|---|---|
| 1020018U | 0h35m | 1h33m |
| 2000047C | 1h02m | 48h50m |
| : : | : : | : : |
| 0320065D | 0h54m | 10h13m |
| : : | : : | : : |
| | | |
| | | |

| Serial Number of Endoscope | Number of Connections | Total Usage of Operating Time |
|---|---|---|
| 1020018U | 6 | 0h40m |
| 2000047C | 18 | 1h05m |
| : : | : : | : : |
| 0320065D | 25 | 1h56m |
| : : | : : | : : |
| | | |
| | | |

ENDOSCOPIC APPARATUS HAVING A PERIPHERAL LIGHT SOURCE

This application is a divisional of 08/760,396, filed Dec. 4, 1999, now U.S. Pat. No. 5,830,121, which is a continuation of 08/330,258, filed Oct. 27, 1994, now abandoned.

BACKGROUND OF THE INVENTION

1. Field of the Invention

The present invention relates to an endoscopic apparatus which includes an endoscope and peripheral device to which the endoscope can be detachably attached.

2. Description of the Related Art

The light source for an endoscope is required to supply light to a light guide and is essential to the endoscope. Further, in the case where the endoscope is a so called electronic endoscope, in which the image is transmitted via electric signals through a solid state image sensor, a video processor for accessing video signals from the solid state image sensor is also essential to the endoscope.

Such support devices such as the light source and video processors described above are themselves expensive and large in size, so an endoscope is detachably attached to such a support (peripheral) device so that various types of endoscopes may be used with a single support device.

Not only is an endoscope susceptible to wear, but it is also inserted into the human body and it is therefore necessary to check the endoscope every 100 hours or once every 50 to 100 uses in order to keep it in perfect working order.

However, since various types of endoscopes are applied to a single light source, a single video processor or the like by replacing one endoscope with another as stated above, it is impossible to calculate the amount of time or the number of times that every endoscope is used with a single light source or a video processor.

Therefore, it is unknown how many hours or how many times each endoscope is used after its initial use or after it is inspected or maintenanced, which sometimes leads to a worn or faulty endoscope being used.

SUMMARY OF THE INVENTION

The primary object of the present invention is to provide an endoscopic device in which the total usage hours and/or number of times used by each endoscope are recorded.

To achieve the object mentioned above, according to the present invention, there is provided an endoscopic apparatus in which an endoscope is detachably attached to a peripheral device essential to the endoscope, the endoscopic apparatus comprising, means for detecting a total duration for the endoscope being in operation, and, storage means for storing the total duration detected by the detecting means.

Preferably the detecting means further comprises means for sensing whether or not the endoscope is in operation, and means for measuring the current duration every time the sensing means senses that the endoscope is in operation.

There is further provided an embodiment which has detecting means further comprising means for sensing whether or not the endoscope is in operation, and means for counting a number of times that the endoscope is in operation.

The present disclosure relates to subject matter contained in the Japanese patent application Nos. 05-268472 (filed on Oct. 27, 1993), 05-276313 (filed on Nov. 5, 1993), 06-167755 and 06-167756 (both filed on Jul. 20, 1994) which are expressly incorporated herein by reference in its entirety.

BRIEF DESCRIPTION OF THE DRAWINGS

The invention will be described below in detail with reference to the accompanying drawings, in which;

FIG. 10 shows a schematic view of a RAM according to the second embodiment;

DESCRIPTION OF THE PREFERRED EMBODIMENT

An endoscopic system according to an embodiment of the present invention will be explained with reference to the drawings.

Figure 1:
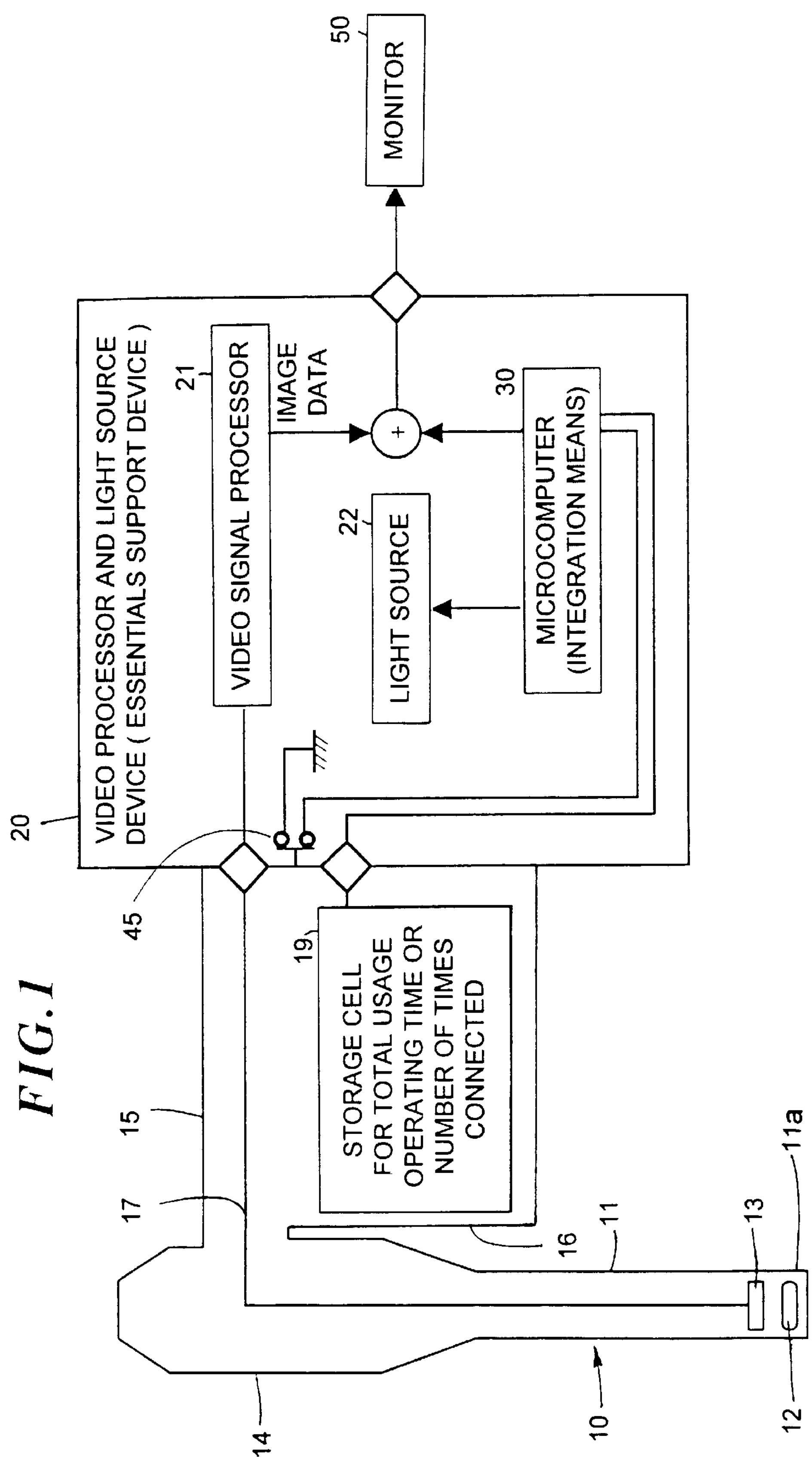
FIG. 1 shows a schematic view of the overall endoscope device according to an embodiment of the present invention.

FIG. 1 is a schematic view of the overall configuration of the endoscope system. Reference numeral 10 is an endoscope. An operating portion 14 with operating devices is connected to the base of a flexible insertion portion 11 with a built-in objective optical system 12, and a solid-state image sensor 13 and the like at the tip 11*a* thereof. Further, a connector 16 at the tip of a flexible connecting tube 15 is removably connected to a video processor and light source device 20.

In the connection tube 15, a light guide fiber bundle (not shown) for transmitting light for lighting the subject and a signal cable 17 for transmitting video signals from the solid-state image sensor 13 are inserted and connected to the connector 16. A storage cell 19 comprising an electrically erasable programmable read only memory (EEPROM), for example, is built into the connector 16.

In the video processor and light source device 20, a light source 22 for supplying light to the light guide fiber bundle, a video signal processor 21 for processing video signals transmitted from the solid-state image sensor 13, and controller 30 with a microcomputer for various controls (hereinafter merely referred to as "microcomputer") are accommodated.

As a result, in order to use the endoscope 10, the connector 16 is always connected to the video processor and light source device 20, and since it is required to clean and disinfect the endoscope 10 in a disinfectant after use, the connector 16 is always disconnected from the video processor and light source device 20 after each use of every endoscope.

Numeral 50 shows a monitor for reproducing visible images from the image signals which are transmitted from the solid state image sensor 13. The endoscope system is further provided with an air tube, a water tube, and a suction tube (not shown).

Figure 2:
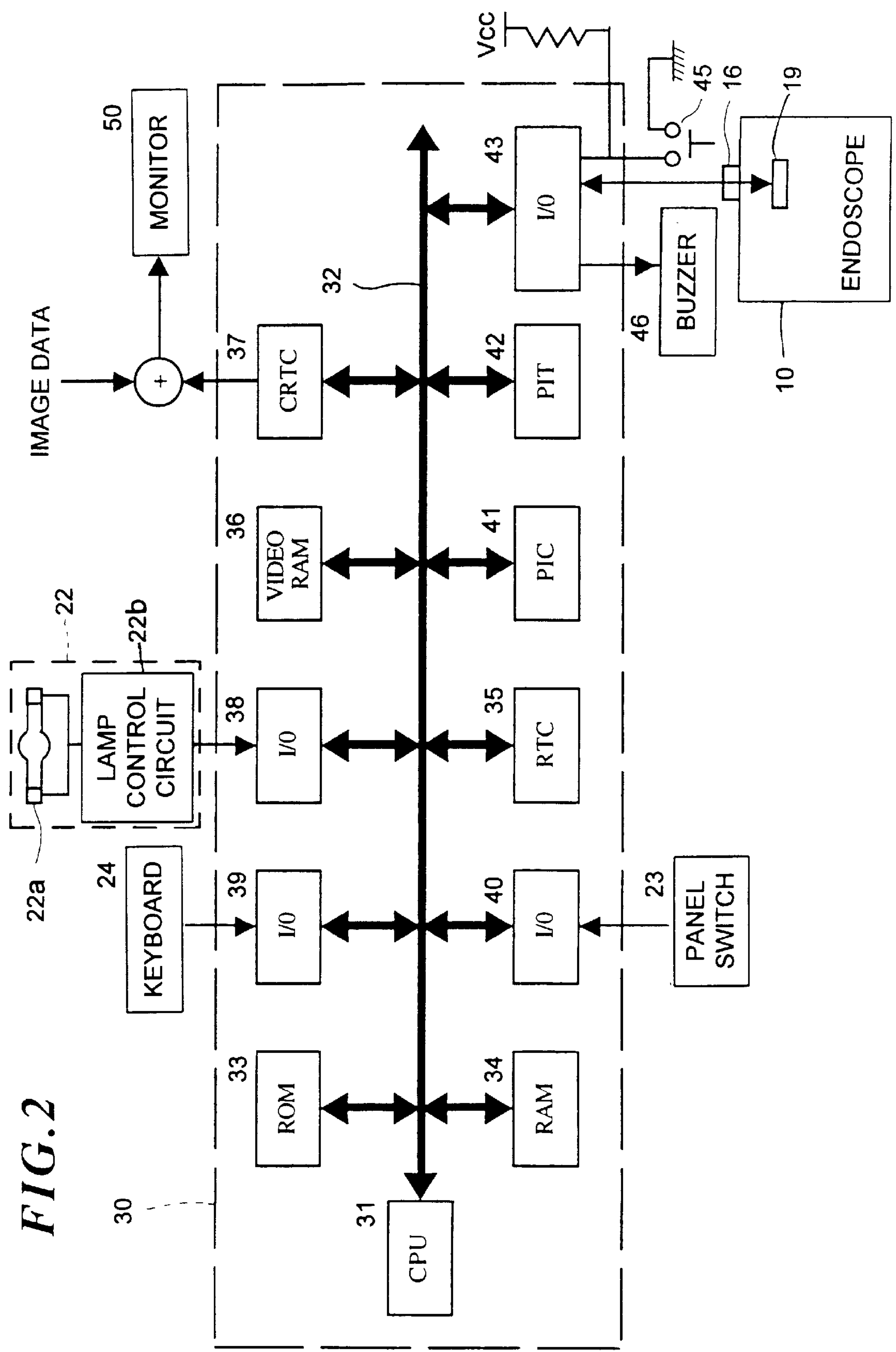
FIG. 2 shows a block diagram of a control circuit according to the embodiment.

FIG. 2 is the microcomputer 30 in the video processor and light source device 20 and peripheral device therefor for controlling the brightness of the light source bulb 22*a*, images displayed on the monitor 50, and superimposition of date on the display.

A system bus 32 is connected to a central processing unit (CPU) 31. A read only memory (ROM) 33 in which programs and the like are installed, a random access memory (RAM) 34 and a real time clock (RTC) 35 are connected to the system bus 32.

Character data for display installed in a video random access memory (video RAM) 36 and the image data outputted from the video signal processor 21 are synthesized by the CRT controller (CRTC) 37 connected to the system bus 32 and outputted to the monitor 50.

A panel switch 23 of the video processor and light source device 20, a lamp control circuit 22*b* for controlling the light source lamp 22*a*, and a keyboard 24 are connected to each other through input/output ports 40, 38 and 39 respectively. Numeral 41 is a programmable interruption controller (PIC) and numeral 42 shows a programmable interval timer (PIT).

To the input/output port 43, to which the connector 16 of the endoscope 10 is connected, is further connected the storage cell 19 in the endoscope 10 via the connector 16 to serially transmit and receive data.

A switch 45 connected to the input/output port 43 is depressed by connecting the connector 16 to the video processor and light source device 20; the corresponding terminal turns to low level, which causes the connection of the endoscope 10 to be detected. Numeral 46 shows an alarm buzzer.

Data indicating the type of endoscope in operation is installed in the storage cell 19 which is built into the connector 16 of the endoscope 10 in advance. Further, the connector 16 is connected to the video processor and light source device 20, and the total usage operating time while the light source lamp 22*a* is switched on, that is, the time that the endoscope 10 is in service is stored. Then, the total usage operating time is displayed on the monitor 50. When the total usage operating time of the endoscope 10 reaches a standard time between maintenance value, the alarm 46 is actuated. The above operation and control method will be explained below.

Figure 3:
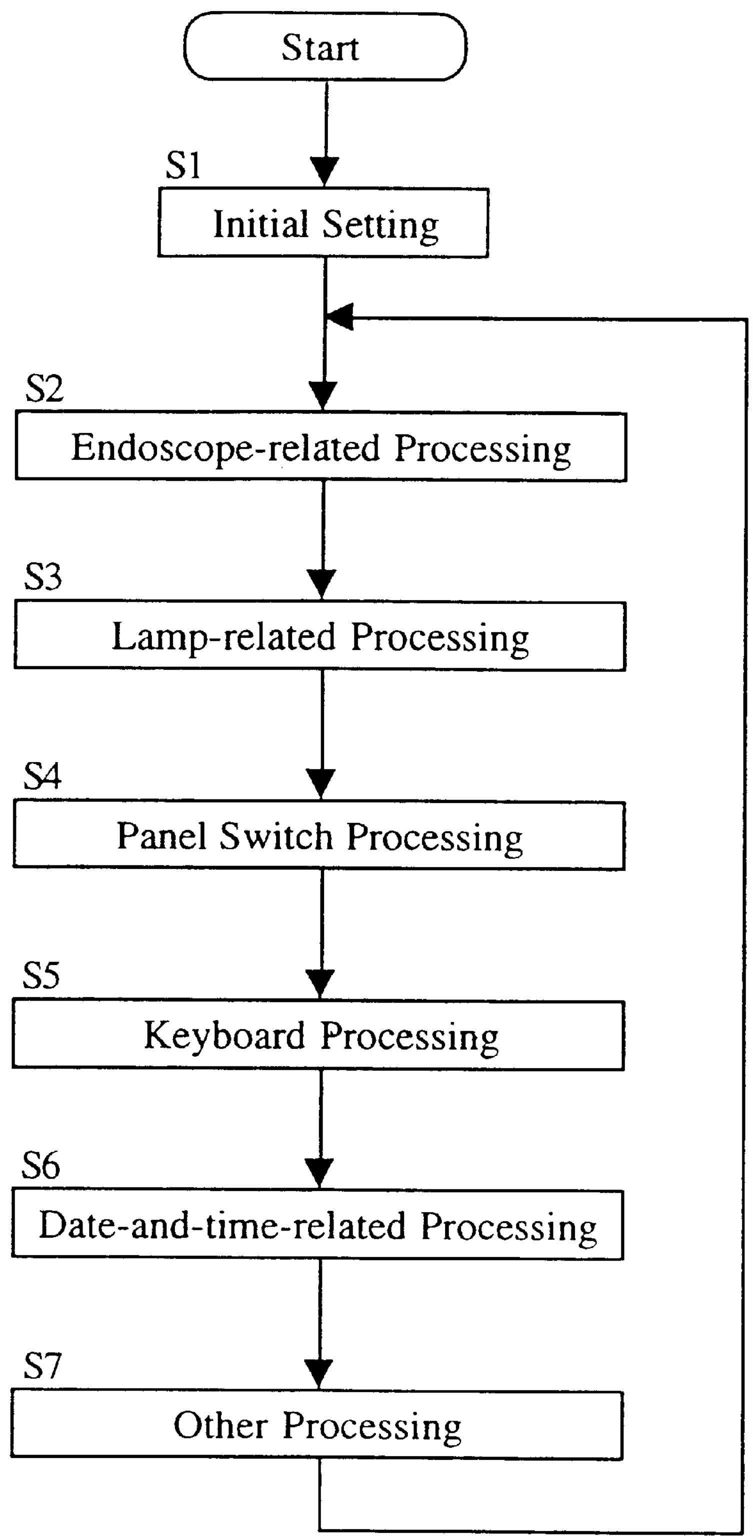
FIG. 3 shows a flow chart of a main program of the control process according to the embodiment.
Figure 4:
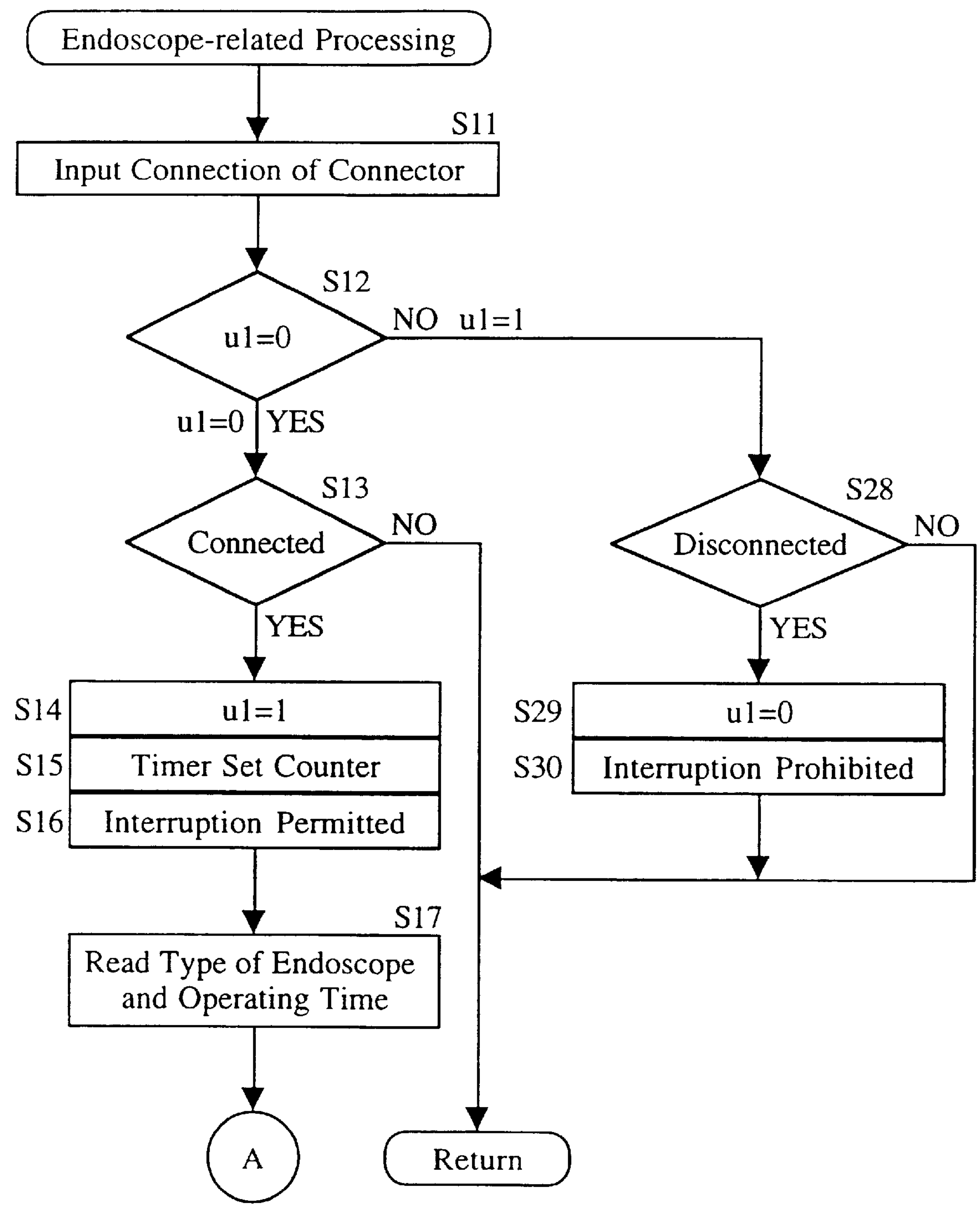
FIG. 4 shows a part of a flow chart of a program of an endoscope-related process according to the first embodiment.
Figure 5:
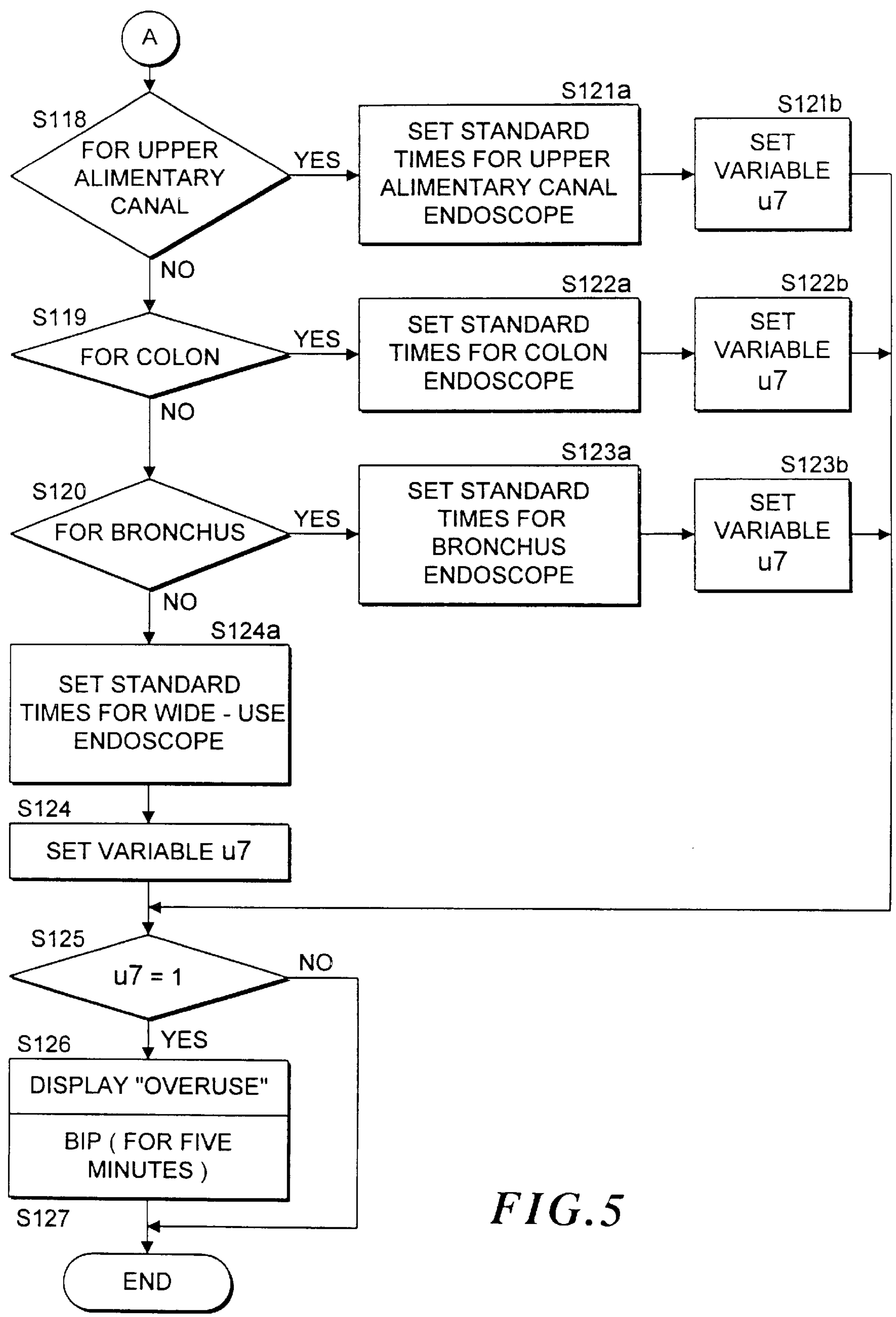
FIG. 5 shows a part of the flow chart of the program of the endoscope-related process according to the first embodiment.

FIGS. 3–5 are flow charts showing the content of the main program installed in the ROM 33 of the microcomputer 30. In the flow chart, "S" indicates the step processed.

Reference symbols u1 and u3 are variables (flags) for classifying programs. The variable "u1" shows whether or not the connector 16 of the endoscope 10 is connected to the video processor and light source device 20 ("u1=1" means connected and "u1=0" disconnected). The variable "u3" is use to shows whether or not to indicate a total operating time of the endoscope 10 exceeds a standard value ("u3=1" is displayed and "u3=0" not displayed).

After the initial setting such as "u1=0" at step S1, an endoscope-related process is executed at step S2. The content of the process will be explained in detail with reference to FIG. 4 and following figures. After the endoscope-related process at step S2, lamp-control-circuit-related processing is executed at step S3 and the process set by the panel switch 23 is executed at step S4.

After the panel-switch processing at step S4, input processing from the keyboard 24 at step S5, the date-and time display processing at step S6 and other processing at step S7 are executed, and the sequence returns to the endoscope-related processing at step S2 to repeat the above process.

FIGS. 4 and 5 are flow charts showing the content of the endoscope-related process at step S2.

At first, the condition of the input/output port 43 to which the connector 16 of the endoscope 10 is connected is inputted at step S11. Then, whether or not the variable u1 is zero is judged at step S12.

If u1=0 at step S12, which means the connector 16 was not connected to the video processor and light source device 20 immediately after the initial setting or at the last checking, whether the connector 16 is connected to or disconnected from the video processor and light source device 20 is judged based on whether the connector input terminal of the input port 43 is at a high level or at a low level at step S13. Subsequently, if the connector 16 is disconnected, "0" is set to u1 and interruption is prohibited to finish the endoscope-related processing at S2; then the sequence advances to the lamp-related processing at step S3.

If the connector 16 is judged to be connected at step S13, the variable u1 is set to 1 at step S14, the counter of the programmable interval timer (PIT) 42 is set at step S15, and the interruption flag of the programmable interruption controller (PIC) 41 is reset to allow the interruption at step S16.

Figure 6:
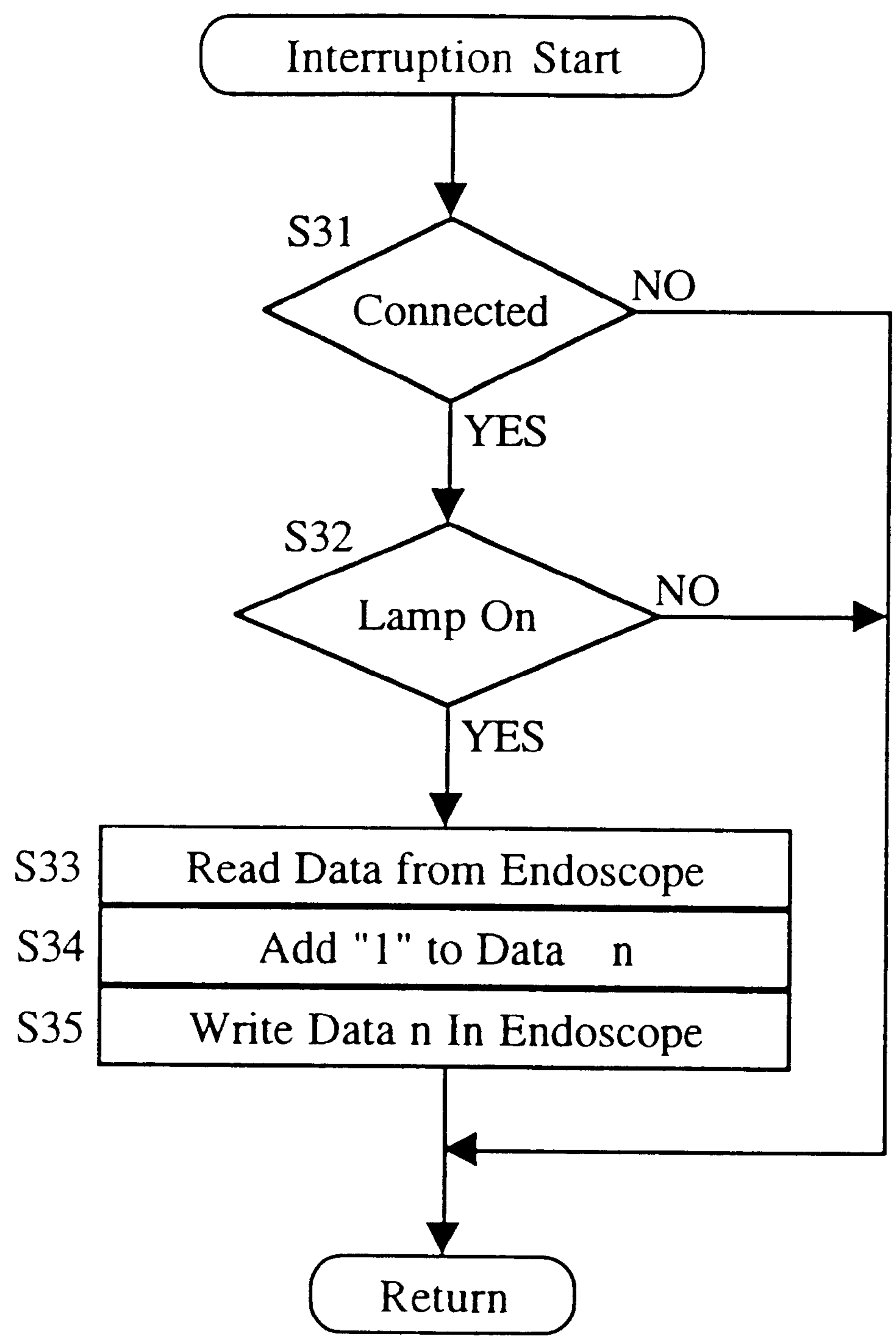
FIG. 6 shows a flow chart of a program of an interruption process according to the first embodiment.

The interruption process is executed every seven-and-half minutes, for instance, by the PIC 41 and PIT 42 based on the program described by the flow chart in FIG. 6. In this process, for caution's sake as at step S13, whether or not the connector 16 of the endoscope 10 is connected to the video processor and light source device 20 is judged at step S31. This step S31 is executed as a precaution and is therefore negligible.

Subsequently, the connector 16 is disconnected and the interruption is finished without execution. To the contrary, if the connector 16 of the endoscope 10 is connected to the video processor and light source device 20, whether or not the light source lamp 22*a* is turned on is checked at step S32, and the interruption is completed unless the lamp 22*a* is turned on.

At step S32, if the light source lamp 22*a* is turned on, the endoscope 10 is in service; therefore number of n units of time data is read from the storage cell 19 of the endoscope 10 at step S33 and "1" is added to number of n at step S34; the result is written in the storage cell 19 of the endoscope 10 at step S35. As described above, the total number of n units of time for the endoscope 10 is stored in the storege cell 19 after each 7.5 min. period that the endoscope has been used the number is incremented by "+1 (1 is added)".

Referring to FIGS. 4 and 5 again, immediately after the interruption is permitted at step S16, the type of endoscope 10 in operation and the operating time of the endoscope 10 are read from the storage cell 19 of the endoscope 10 at step S17.

Figure 7:
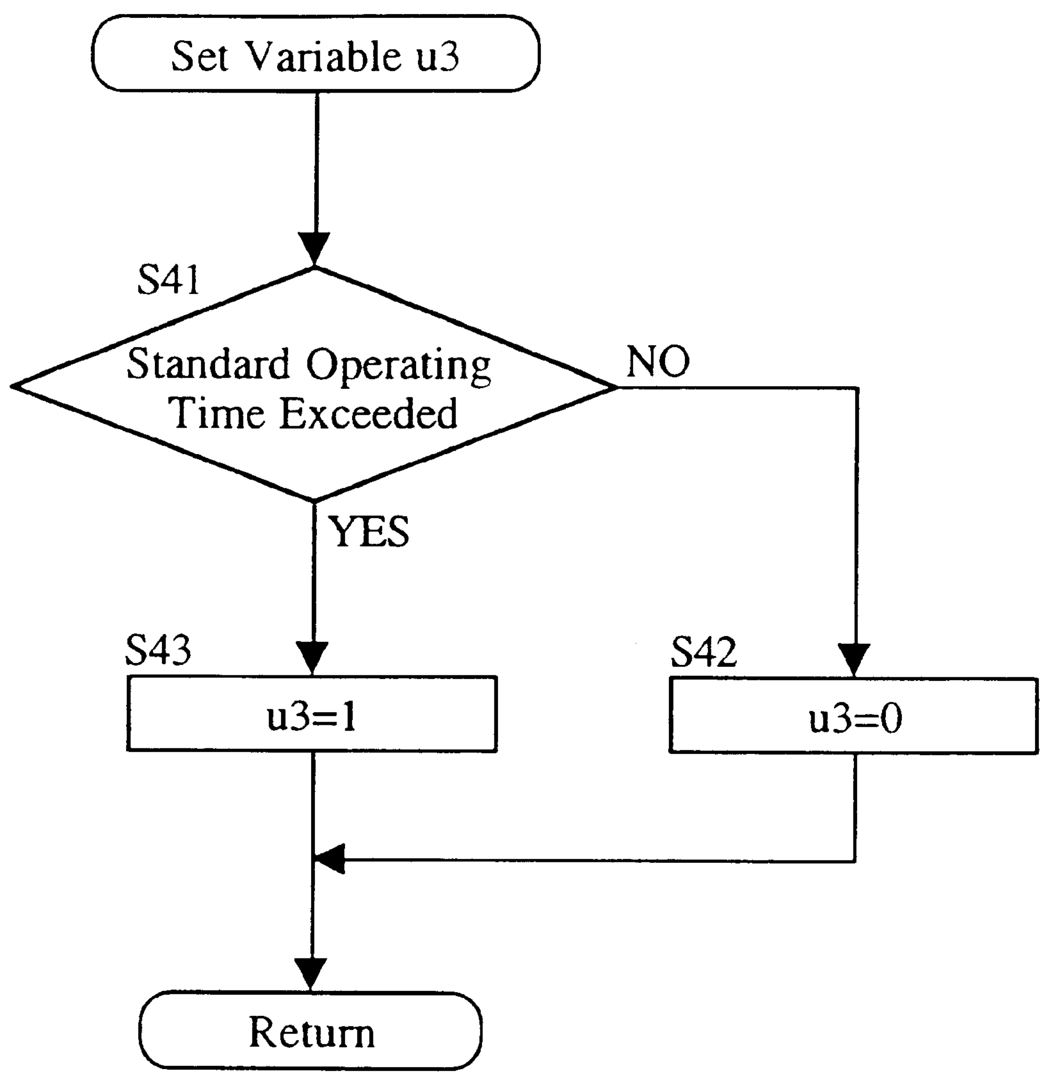
FIG. 7 shows a flow chart of a part of the endoscope-related process program according to the first embodiment.

Then, the standard time between maintenance value and the variable u3 are set in accordance with the type of endoscope 10 at steps S18 to S24. The setting of the variable u3 is executed based on the program shown in the flow chart in FIG. 7. At first, whether or not the total usage operating time exceeds the standard time between maintenance value is checked at step S41.

The standard value varies with the type of endoscope used, i.e. for the upper alimentary canal, colon, or other special purpose. The result of the judgment of type of endoscope at steps S18 to S20 gives different standard operating time at steps S18, S21, S19, S22a, S20 and S23a.

Unless the total usage operating time reaches the standard time between maintenance value, the variable u3 set to zero at step S42. To the contrary, if the total usage operating time reaches the standard time between maintenance value, u3 is set to "1" at step S43.

Figure 8:
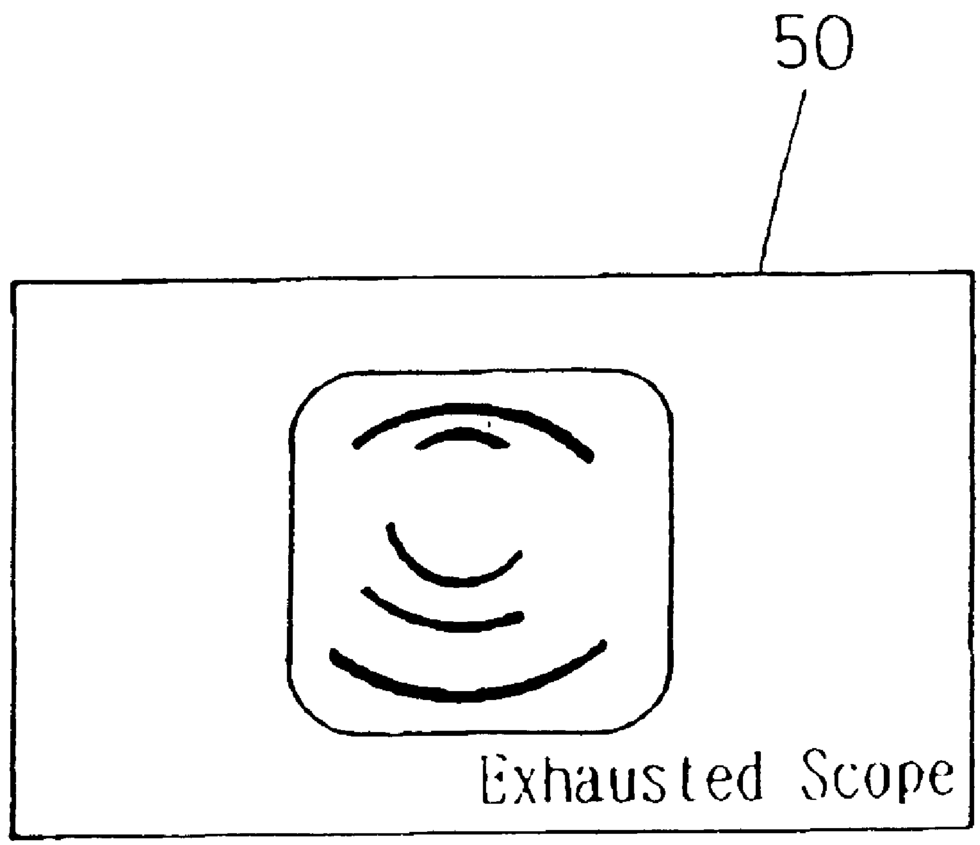
FIG. 8 shows is a schematic view of the picture of a monitor according to the first embodiment.

After the variable u3 is set, referring to FIGS. 3 and 4 again, whether or not the variable u3=1 is judged at step S25. If the variable u3 is not "1", the sequence advances to the lamp-related process at step S3. If the variable u3 is "1", as illustrated in FIG. 8, overuse of the endoscope is displayed on the monitor 50 at step S26 and the alarm buzzer 46 is simultaneously actuated for five seconds for example, then the sequence advances to the lamp-related process at step S3.

As described above, the integrated operating time of the endoscope 10 is compared with the standard value based on the type of endoscope. When exceeding the standard operating time, the result is displayed on the monitor 50 and the alarm buzzer 46 is actuated at step S27.

If the variable u1 is not "0" at step S12, which means it is not just after the initial setting and the connector 16 was connected to the video processor and light source device 20 at the last checking, whether or not the connector 16 is disconnected from the video processor and light source device 20 is checked at step S28 as at step S13.

Then, if the connector 16 is judged to be connected also, the sequence immediately advances to the lamp-related process at step S3. To the contrary, if the connector 16 is disconnected, the variable u1 is set to zero at step S29 and the interruption is prohibited at step S30, then the sequence advances to the lamp related process at step S3.

In this embodiment, the total usage operating time of the endoscope 10 can be displayed on the monitor 50. However, whether the result is to be displayed on the monitor 50 or not is choosable through the eighth key F8 of function keys on the keyboard not shown.

Figure 9:
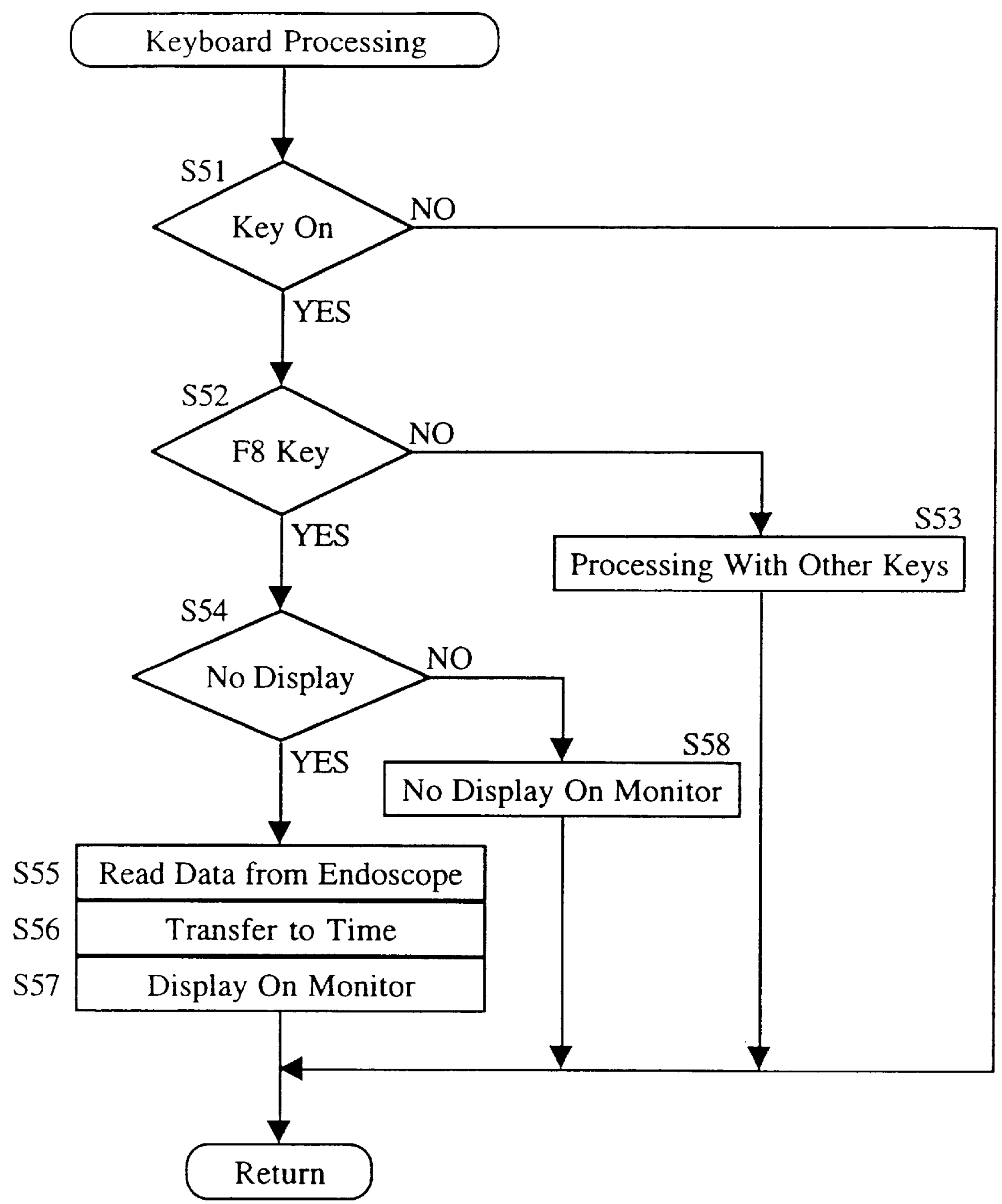
FIG. 9 shows a flow chart of a keyboard processing program according to the first embodiment.
Figure 11:
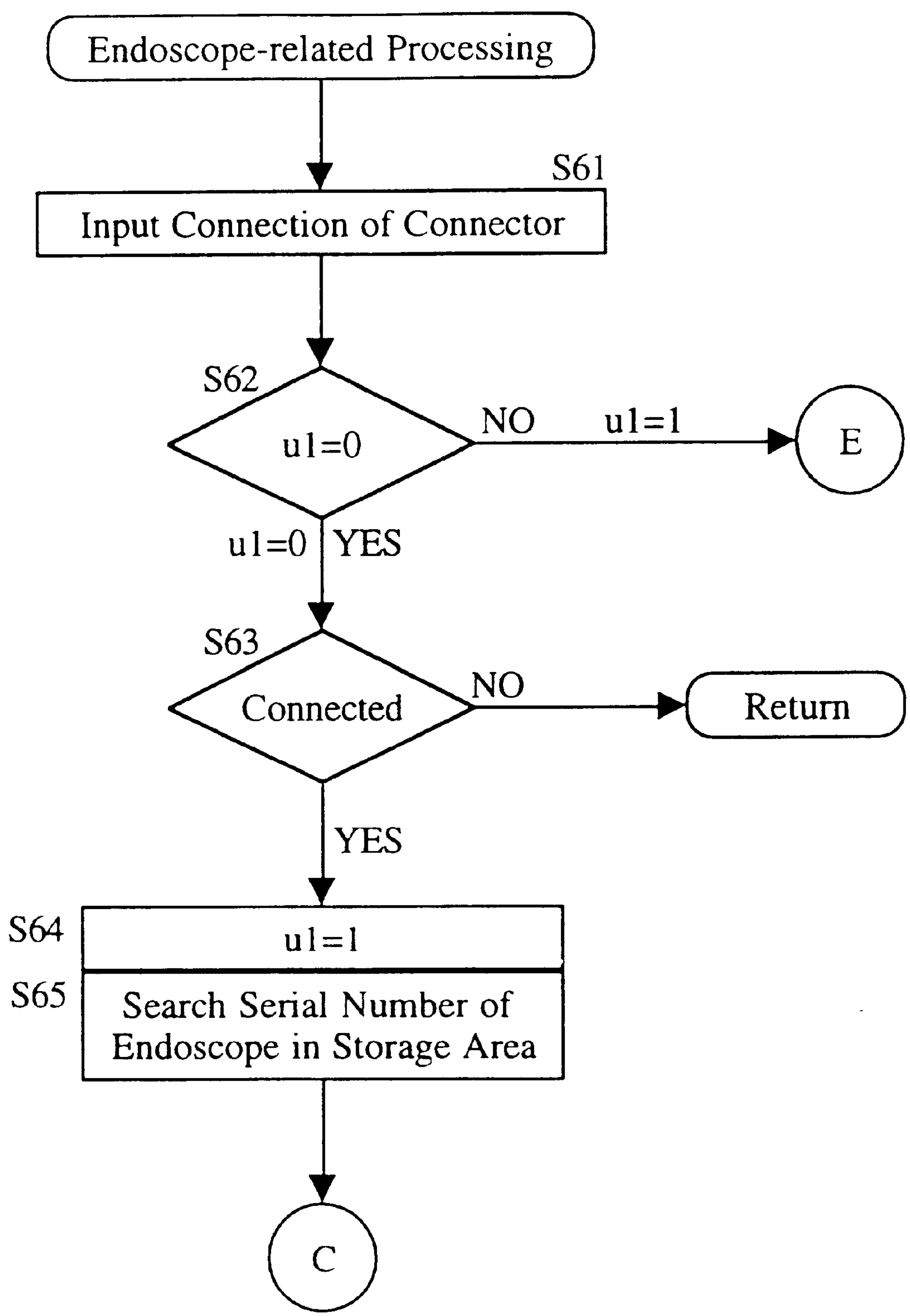
FIG. 11 shows a part of a flow chart of the endoscope related process program according to the second embodiment.

FIG. 9 is a flow chart showing the content of the program for switching the display of the integrated operating time as one of the processes of keyboard at step S5. In this step, whether or not any key of the keyboard 24 is depressed is checked first, and if no key is depressed, the processing of key board at step S5 is finished and the sequence advances to the date and time related process at step S6.

If any key of the keyboard is depressed, whether or not the depressed key is the eighth key F8 is checked at step S52. Unless the key is F8 key, the processing corresponding to the depressed key is executed at step S53 and the sequence advances to the date and time related process at step S6.

If the F8 key is switched on, whether or not the integrated operating time is already displayed on the monitor 50 is judged at step S54, and if so, the indication is erased at step S58 and the sequence advances to the date and time related process at step S6.

If the total usage operating time is not displayed on the monitor 50, the total usage operating time is read from the storage cell 19 of the endoscope 10 at step S55, and the data is converted into the amount of time at step S56 to display it on the monitor 50 at step S57, and then the sequence advances to the date and time related process at step S6.

In the conversion at step S56, the interruption for adding "1" to the data on the service of the endoscope is executed once per seven-and-half minutes (eight times an hour), so the data on the operating time is set to "n" represents the number of interruption loop cycles, the total usage operating time that the endoscope is in service equals n/8 hours or 7.5×n minutes.

Next, the endoscope-related process at step S2 according to the second embodiment of the present invention will be explained. In this embodiment, the serial number of the endoscope 10 is installed in the storage cell 19 of the endoscope 10 in advance. The total usage operating time of the endoscope 10 measured with the timer (RTC) 35, and the count (one hour) is also stored in the storage cell 19.

As illustrated in FIG. 10, the RAM 34 of the video processor and light source device 20 is provided with a storage area where the serial number of the connected endoscope 10 and the operating time for its single usage are written as a data set, and the stored data is sustained using a cell or the like. The data may be written to a recording media such as a magnetic recording media including a hard disk. In this embodiment, no interruption is executed to calculate the total usage operating time of the endoscope, so the PIC 41 and PIT 42 are unnecessary.

Valuables u1 and u5 are used for classifying programs, and the variable u1 is similar to that used in the first embodiment. The variable u5 is set to "1" when the connector 16 is connected to the video processor and light source device 20 and the light source lamp is turned on, and the variable u5 is set to zero in other cases.

FIGS. 11 to 14 are flow charts showing programs for the endoscope related process at step S2 in the second embodiment. The content of programs other than main program is the same as those of the first embodiment.

The same processes as at steps S11 to S13 of the first embodiment are executed at steps S61 to S63. Then, if the connector 16 is judged to be disconnected from the video processor and light source device 20 at step S63, the sequence immediately advances to the lamp-related process at step S3.

To the contrary, if the connector 16 is judged to be connected to the video processor and light source device 20 at step S63, the variable u1 is set to "1" at step S64, and the serial number of the endoscope in the storage area of the RAM 34 is searched for at step S65, and then the serial number of the endoscope 10 connected at that time is read from the storage cell 19 for comparison at step S66.

Then, if the serial number of the endoscope 10 in operation is stored in the storage area of the RAM 34, the amount of time that the endoscope has been used (operating time at last single usage) which is stored in the RAM 34 is added to the total usage operating time in the storage cell 19 of the endoscope 10, and the operating time stored in the RAM 34 is reset to zero at step S67. Further, when the number of the endoscope 10 in service is not stored in the storage area of the RAM 34, the number of the endoscope is written in a vacant area of the RAM 34 at step S68.

Subsequently, whether the light source lamp 22*a* is turned on or not is checked at step S69. If the lamp 22*a* is turned off, the variable u5 is set to zero at step S72, and the sequence advances to the lamp-related process at step S3. To the contrary, the light source lamp 22*a* is turned on, the variable u5 is set to "1" at step S 70; the present time is read from the RTC 35 and is stored at step S71; and the sequence advances to the lamp-related process at step S3.

If it is judged at step S62 that the variable u1 is not zero, which means the connector 16 is connected to the video processor and light source device 20 at the last checking but immediately after initial setting, as at step S28, whether or not the connector 16 is disconnected from the video processor and light source device 20 is checked at step S73.

Subsequently, if the connector 16 is disconnected, the operating time at that time is calculated by RTC 35 at step S74, and the operating time is written in an address of the RAM 34 corresponding to the number the endoscope in service at step S75. Then, both variables u1 and u5 are set to zero and the sequence advances to the lamp-related process at step S3. The present operating time is obtained at step S74 by calculating the interval between the time starting the lighting stored in steps S71 or S80 and the present time.

If the connector 16 is judged to be connected at step S73 also, whether or not the variable u5 is zero is checked at step S77. If the variable u5 is zero and the light source lamp 22*a* is turned off at step S78, the sequence immediately advances to the lamp-related process at step S3. To the contrary, if the light source lamp 22*a* is turned on, the variable u1 is set to "1" at step S79; and the time is stored at step S80; and the sequence advances to the lamp-related process at step S3.

If the variable u5 is not zero at step S77, and unless the light source lamp 22*a* is turned on at step S81, the sequence soon advances to the lamp-related process at step S3. To the contrary, if the lamp 22*a* is turned on, the variable u5 is set to "1" at step S79; the present operating time is calculated at step S82; the data is written in the RAM 34 as at steps S74 and S75; and the sequence advances to the lamp-related process at step S3.

The present invention is not limited to the above embodiments and a part or all of integration means for calculating the total usage operating time may be mounted on the endoscope side for example. Further, the total usage operating time storage means for storing total usage operating time may be mounted on the side of the support device such as the video processor or light source device.

With the construction described above, the operating time for each endoscope for a variety of types of endoscopes are read at once from the total usage operating time storage means without having to connect each endoscope to the support device one by one, and the data is displayed in a table on the monitor or the like, which permits the total usage operating time for each endoscope to be confirmed at a glance.

Figure 15:
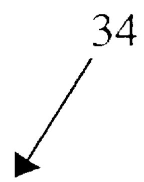
FIG. 15 shows a schematic view of the storage area of a RAM according to the third embodiment.

For the above purposes, the storage area of the RAM 34 in the microcomputer 30 should be enlarged, for example as illustrated in FIG. 15, and the area where the total usage operating time as well as the operating time for that specific event is stored and prepared in accordance with the serial number of each endoscope.

Figure 12:
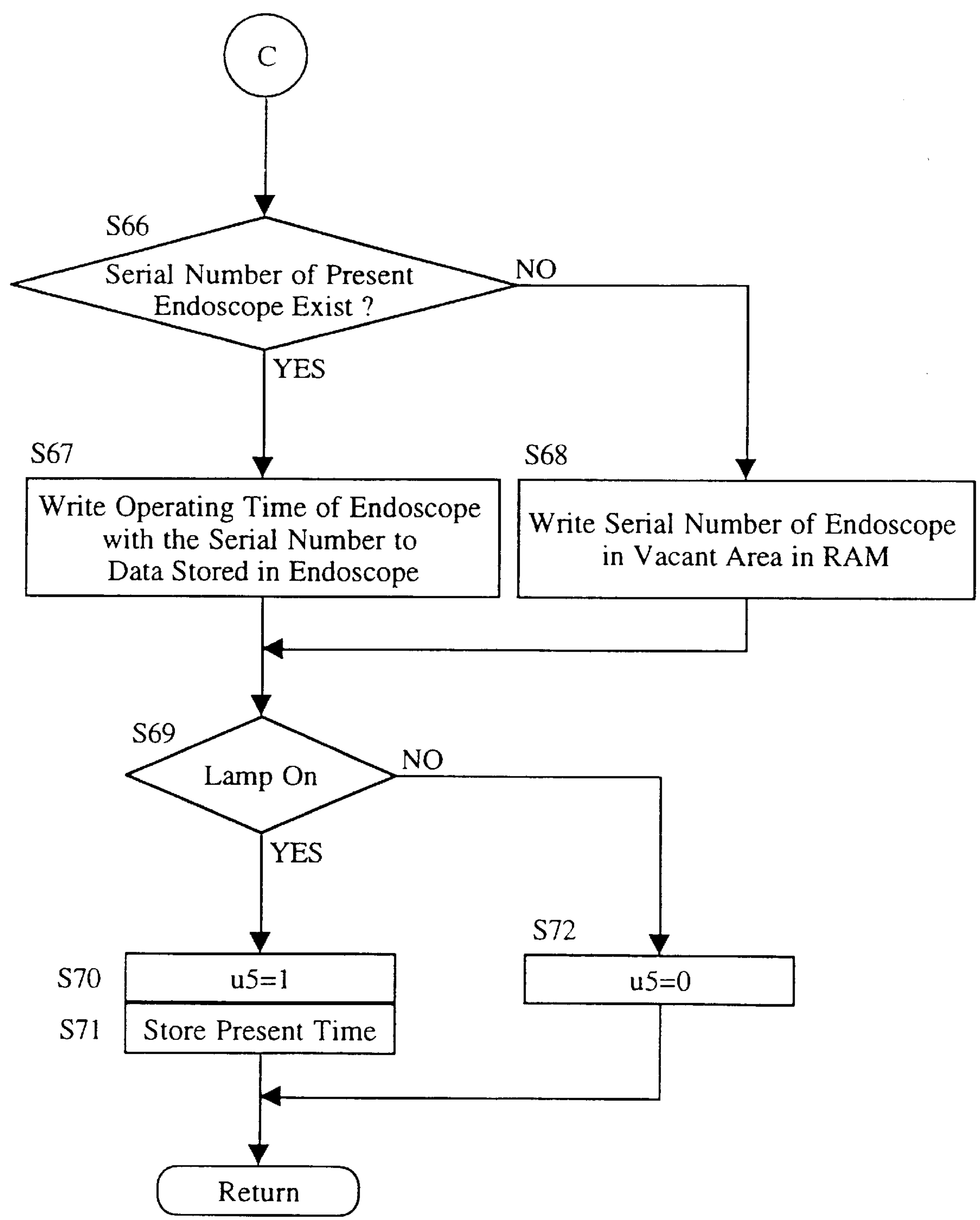
FIG. 12 shows a part of the flow chart of the endoscope-related process program according to the second embodiment.
Figure 13:
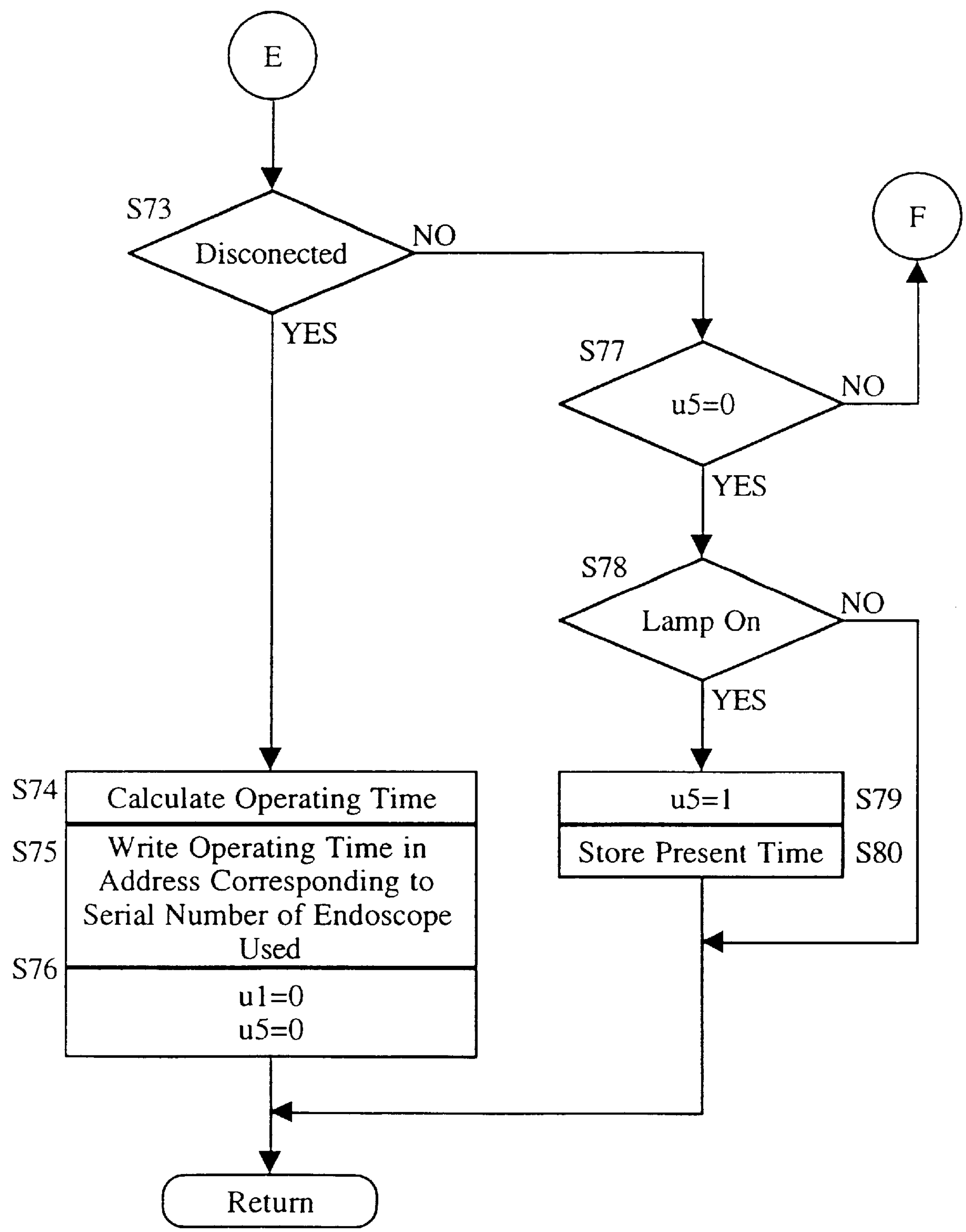
FIG. 13 shows a part of the flow chart of the endoscope-related process program according to the second embodiment.
Figure 14:
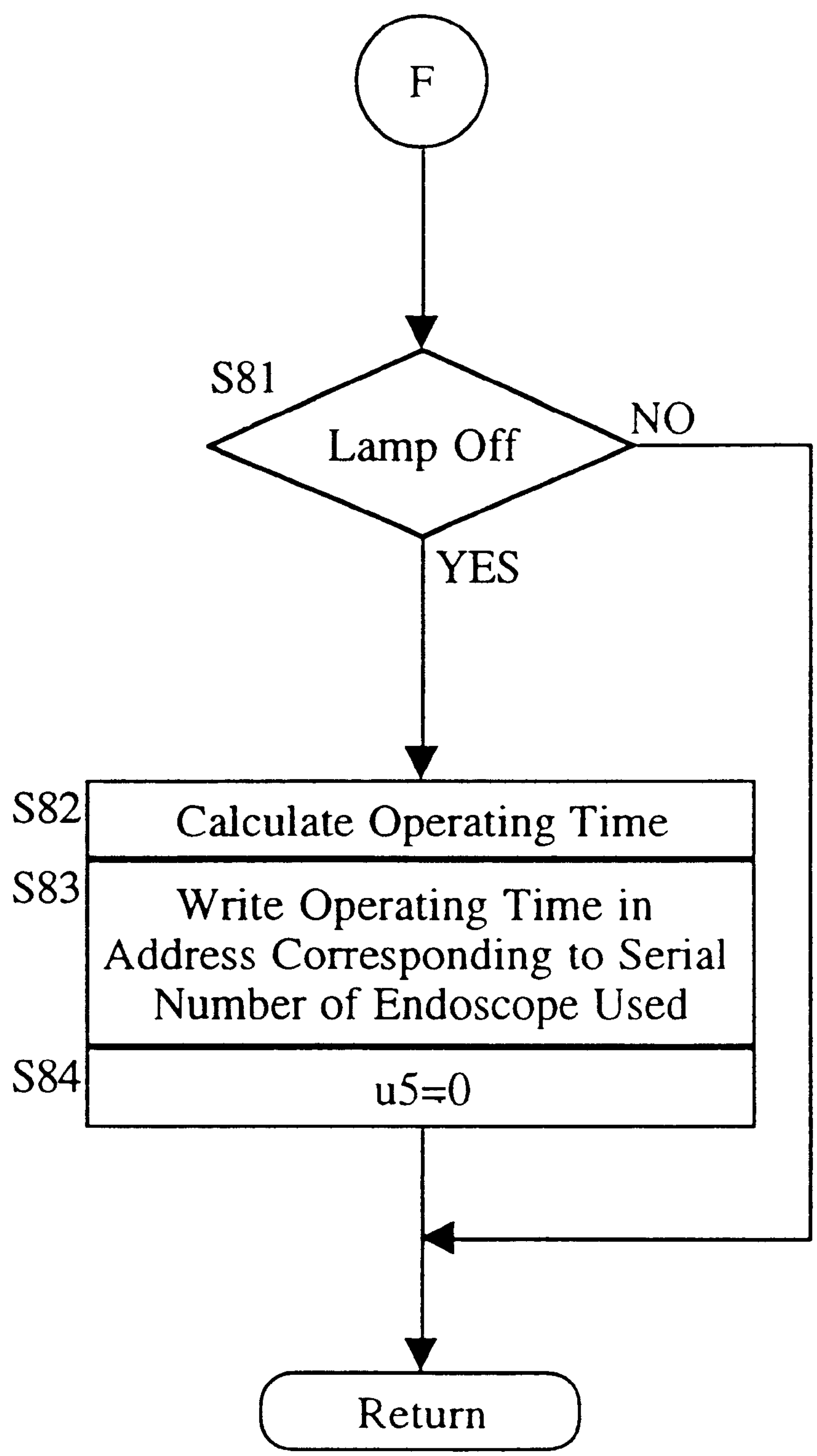
FIG. 14 shows a part of the flow chart of the endoscope-related process program according to the second embodiment.

Then, at the processing step S67 indicated in FIG. 12, the operating time data for that specific event which is stored in the RAM 34 is added to the total usage operating time data in the RAM 34.

With the construction of the endoscope device according to the present invention, since the total usage operating time for each endoscope is stored in the storage cell, the total usage operating time for that endoscope can be displayed, and when it reaches the standard time between maintenance value, the result is displayed and an alarm is actuated, which prevents the overuse of the endoscope in advance. As a result, the failure of the endoscope system or the accidents caused by the system is avoidable through inspection, maintenance and exchange of worn parts.

As a result of employing this apparatus manufacturers of endoscopes will be able to easily gather data on the relationship between total usage time number of operations and types of failure this will contribute greatly to improvements and quality.

In the case where the total usage operating time storage means is mounted on the endoscope side, the total usage operating time of the endoscope can be checked regardless of the support device to which the endoscope is connected. On the other hand, if the total usage operating time storage means is attached to the support device side, the total usage operating time of several endoscopes can be confirmed at a glance with a table without having to connect each endoscope one by one.

In the embodiment described above, total usage operating time of the endoscope is calculated. Next, an endoscope apparatus according to another embodiment of the present invention will be explained. In this embodiment, the number of times that the endoscope is connected to the video processor and light source device is counted. The construction of the endoscope apparatus in this embodiment is the same as the apparatus shown in FIGS. 1 and 2, and a main flow chart of this embodiment is the same as that shown in FIG. 3, therefore the indication thereof will be omitted.

Figure 16:
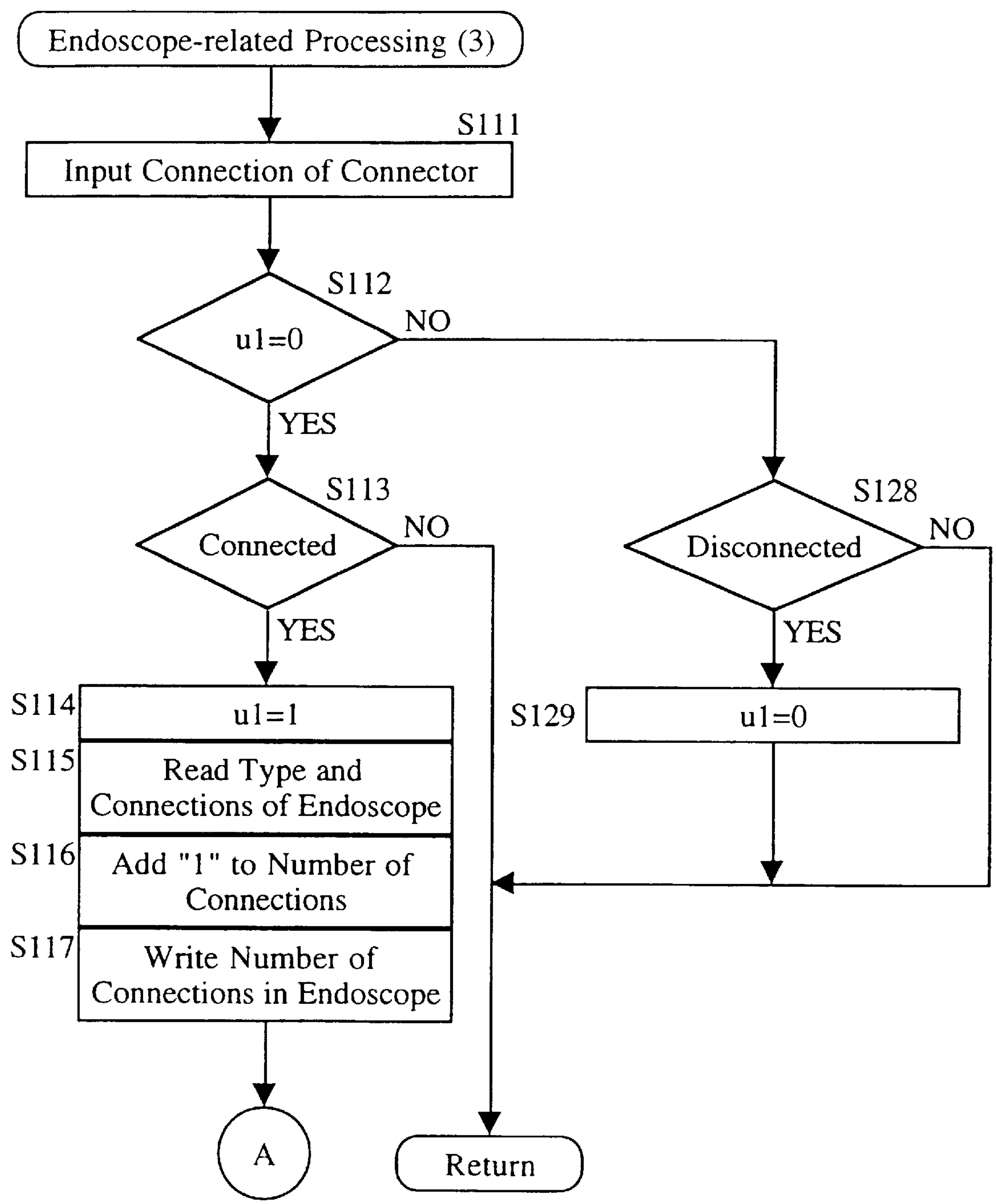
FIG. 16 shows a part of a flow chart of an endoscope-related process program according to the third embodiment.
Figure 17:
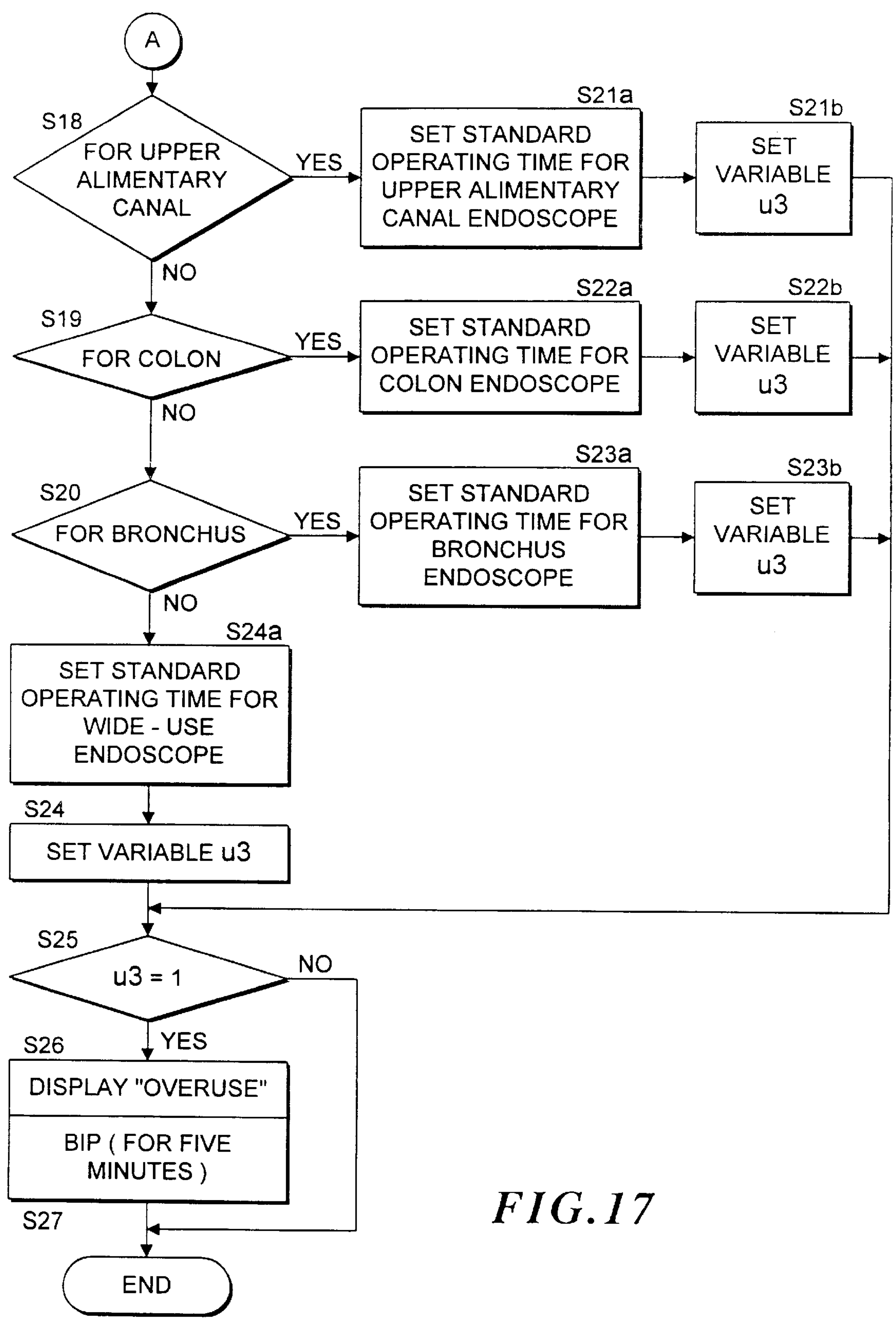
FIG. 17 shows a part of the flow chart of the endoscope-related process program according to the third embodiment.

FIGS. 16 and 17 are flow charts showing the third embodiment of the endoscope-related processing at step S2. In this embodiment, the programmable interrupting controller(PIC) 41 and the programmable interval timer (PIT) 42 are unnecessary to the microcomputer 30, resulting in simple construction.

In this embodiment, firstly, the condition of the input/output ports 43 to which the connector 16 of the endoscope 10 is connected is inputted at step S111. Then, whether or not the variable u1 is zero is judged at step S112.

If the variable u1 is zero at step S112, which means that the connector 16 was disconnected from the video processor and light source device 20, whether or not the connector 16 is connected to the video processor and light source device 20 is judged based on whether the input terminal of the input port 43 is in high level or in low level at step S113. If the connector 16 is disconnected, the endoscope-related processing at step S2 is finished soon, then the sequence advances to the lamp-related process at step S3.

To the contrary, if the connector 16 is connected, a variable u7 is set to "1" at step S114 , and the type and the number of connections for that endoscope 10 in service is read from the storage cell 19 of the endoscope 10 at step S115. Subsequently, "1" is added to the number of times that the endoscope 10 is connected at step S116 to write the result in the storage cell 19 of endoscope 10 at step S117.

Figure 18:
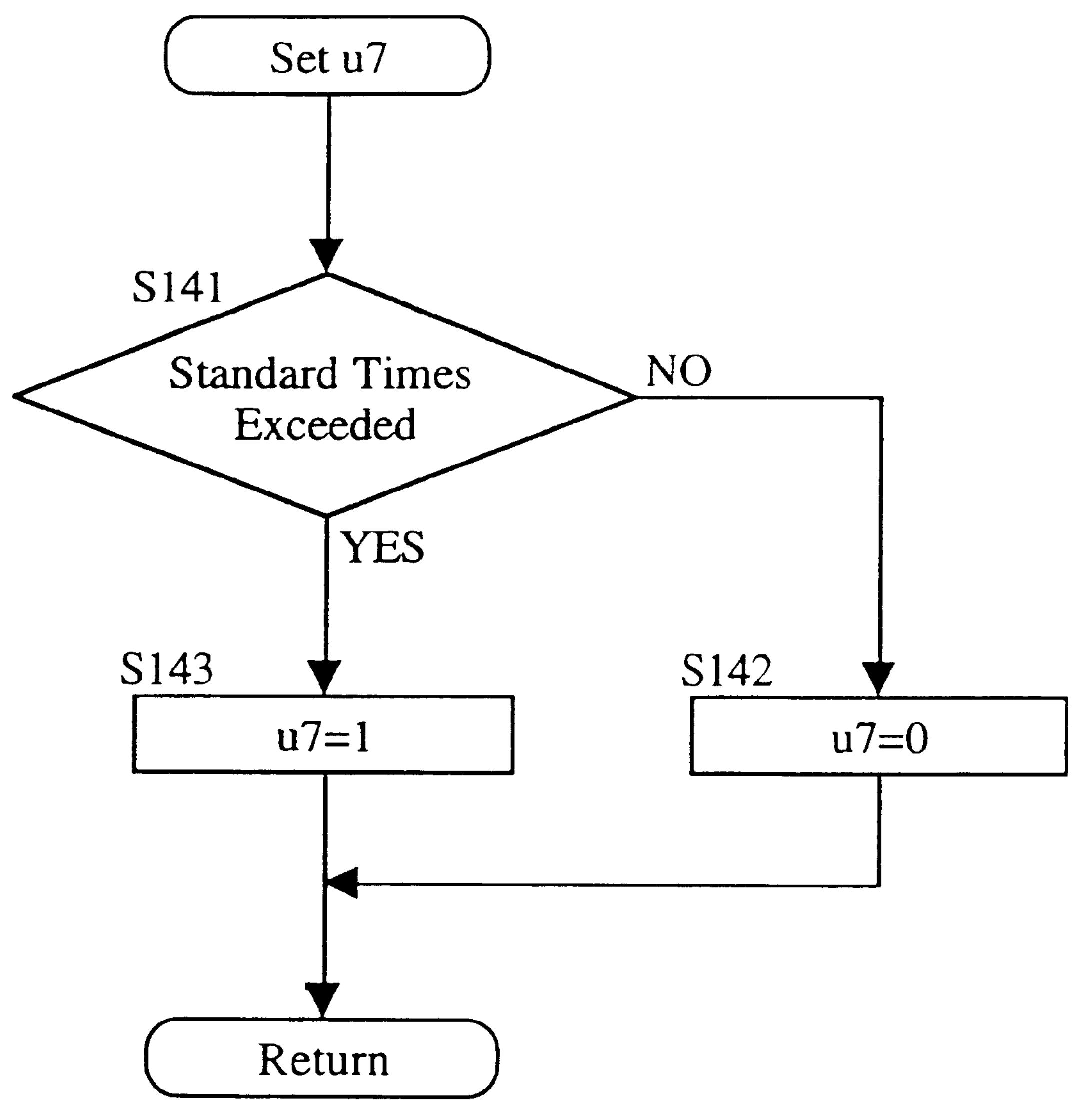
FIG. 18 shows a part of the flow chart of the endoscope-related process program according to the third embodiment.

Subsequently, the variable u7 is set in accordance with the type of endoscope 10 at steps S118 to S124. The variable u7 is set based on the program shown in a flow chart of FIG. 18. Whether or not the number of times that the endoscope 10 is connected is more than the standard maintenance value is checked at step S141.

The standard maintenance value varies with the type of endoscope used, which is judged at steps S118 to S120, i.e. for the upper alimentary canal, colon, bronchus or other special purpose. The result of the judgment of type of endoscope at steps S18 to S20 gives different standard maintenance values.

Unless the number of connections reaches the standard maintenance value, the variable u7 set to zero at step S142. To the contrary, if the number of connections reaches the standard maintenance value, u7 is set to "1" at step S143.

After the variable u7 is set at steps S121 to S124, referring to FIGS. 16 and 17 again, whether or not the variable u7=1 is judged at step S125. If the variable u7 is not "1", the sequence advances to the lamp related process at step S3.

To the contrary, if the variable u7 is "1", as illustrated in FIG. 8, overuse of the endoscope 10 is displayed on the monitor 50 at step S126 and the alarm buzzer 46 is simultaneously actuated for five seconds for example, then the sequence advances to the lamp-related process at step S3.

As described above, the number of connections of the endoscope 10 is compared with the standard maintenance value based on the type of endoscope. When exceeding the standard maintenance value, the result is displayed on the monitor 50 and the alarm buzzer 46 is actuated at step S127.

If the variable u1 is not "1" at step S112, which means it is not just after the initial setting and the connector 16 was connected to the video processor and light source device 20 at the last checking, whether or not the connector 16 is disconnected from the video processor and light source device 20 is checked at step S128 as at step S113.

Then, if the connector 16 is judged to be connected also, the sequence immediately advances to the lamp-related process at step S3. To the contrary, if the connector 16 is disconnected, the variable u1 is set to zero at step S129 and the sequence advances to the lamp-related process at step S3.

In this embodiment, the number of connections of the endoscope 10 can be displayed on the monitor 50. However, whether the result is to be displayed on the monitor or not is changeable through the ninth key F9 (not shown) of function keys on the keyboard 24.

Figure 19:
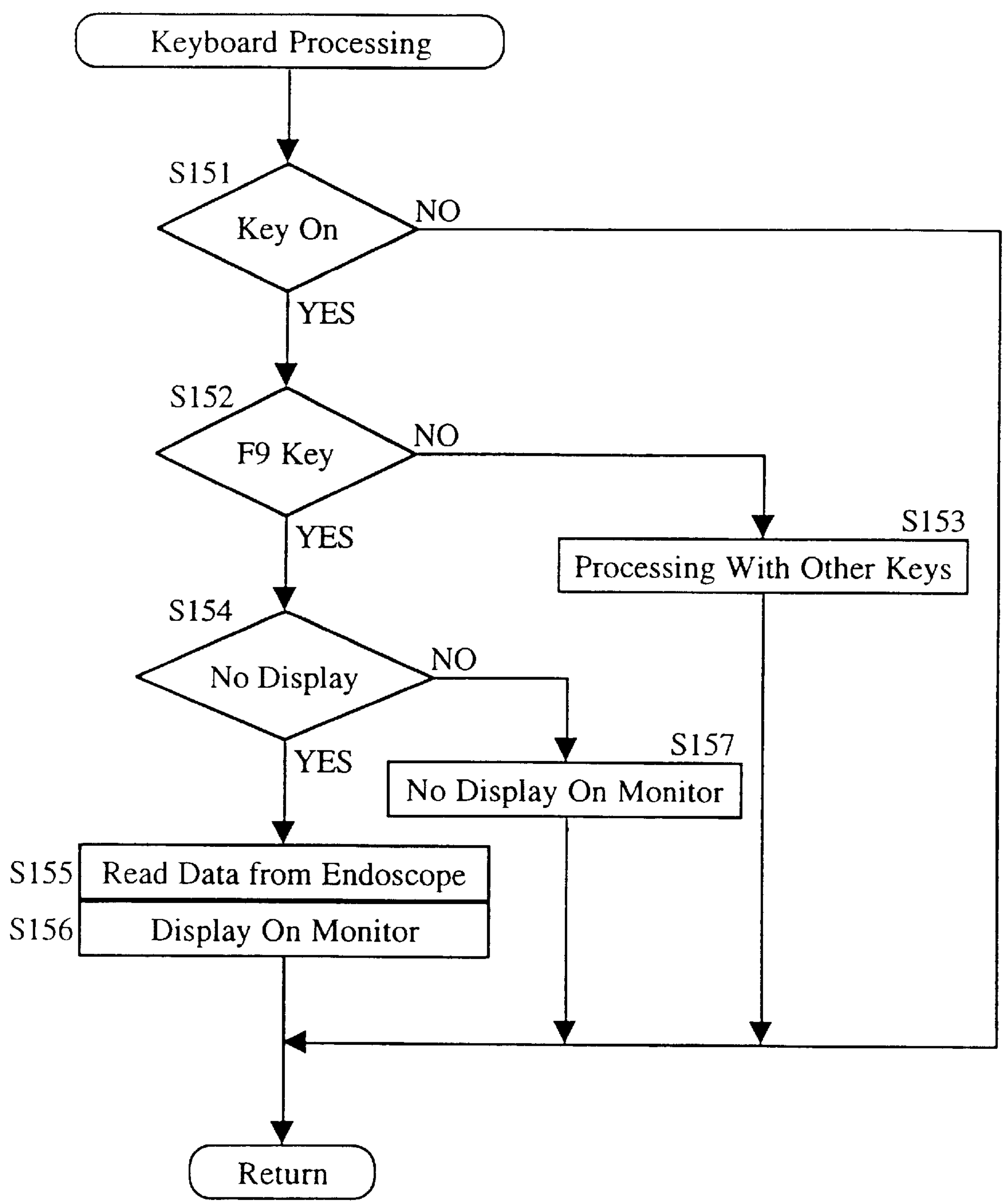
FIG. 19 shows a flow chart of a keyboard processing program according to the third embodiment.

FIG. 19 is a flow chart showing the content of the program for switching the display of the number of connections as one of the processes of keyboard at step S5. In this step, whether or not any key of the keyboard 24 is depressed is checked first at step S151, and if no key is depressed, the processing of key board at step S5 is finished and the sequence advances to the date-and-time-related process at step S6.

If any key of the keyboard 24 is depressed, whether or not the depressed key is the ninth key F9 is checked at step S152. Unless the key is F9 key, the processing corresponding to the depressed key is executed at step S153 and the sequence advances to the date-and-time-related process at step S6.

If the F9 key is switched on, whether or not the number of connections is already displayed on the monitor 50 is judged at step S154, and if so, the indication is erased at step S157 and the sequence advances to the date-and-time-related process at step S6.

If the number of connections is not displayed on the monitor 50, the number of connections is read from the storage cell 19 of the endoscope 10 at step S155, and the data is displayed on the monitor 50 at step S156, and then the sequence advances to date and time related process at step S6.

Figure 20:
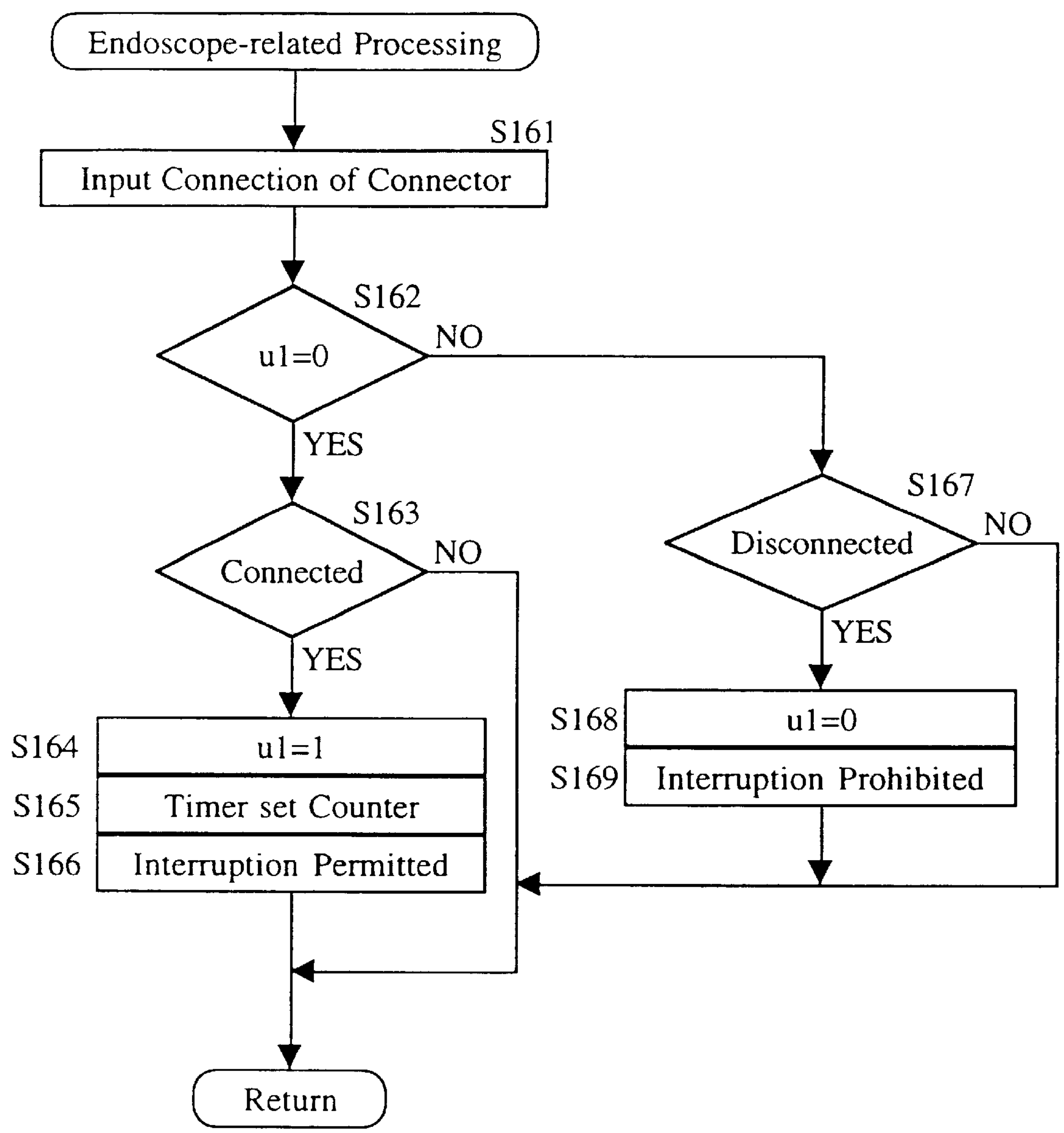
FIG. 20 shows a flow chart of the endoscope-related processing program according to the fourth embodiment.

Next, the fourth embodiment of the endoscope-related processing at step S2 will be explained. In this embodiment, a connecting operation carried out within four minutes of the last use is not counted as one this will exclude connecting or disconnecting operations of the connector 16 not for the purpose of using the endoscope from the connection count processing. FIG. 20 is a flow chart used in this embodiment.

Firstly, the condition of the input/output ports 43 to which the connector 16 of the endoscope 10 is connected is inputted at step S161. Then, whether or not the variable u1 is zero is judged at step S162.

If the variable u1 is zero at step S162, which means that the connector 16 was disconnected from the video processor and light source device 20, whether or not the connector 16 is connected to the video processor and light source device 20 is judged based on whether the input terminal of the input port 43 is at a high level or at a low level at step S163. If the connector 16 is disconnected, the endoscope-related processing at step S2 is finished soon, then the sequence advances to the lamp-related process at step S3.

To the contrary, if the connector 16 is judged to be connected at step S163, the variable u1 is set to "1" at step S164, and the counter of the programmable interval timer (PIT) 42 is set such that the interruption is executed after four minutes at step S165 and the interruption mask of the programmable interruption controller (PIC) 41 is reset to prepare for the interruption at step S166.

Figure 21:
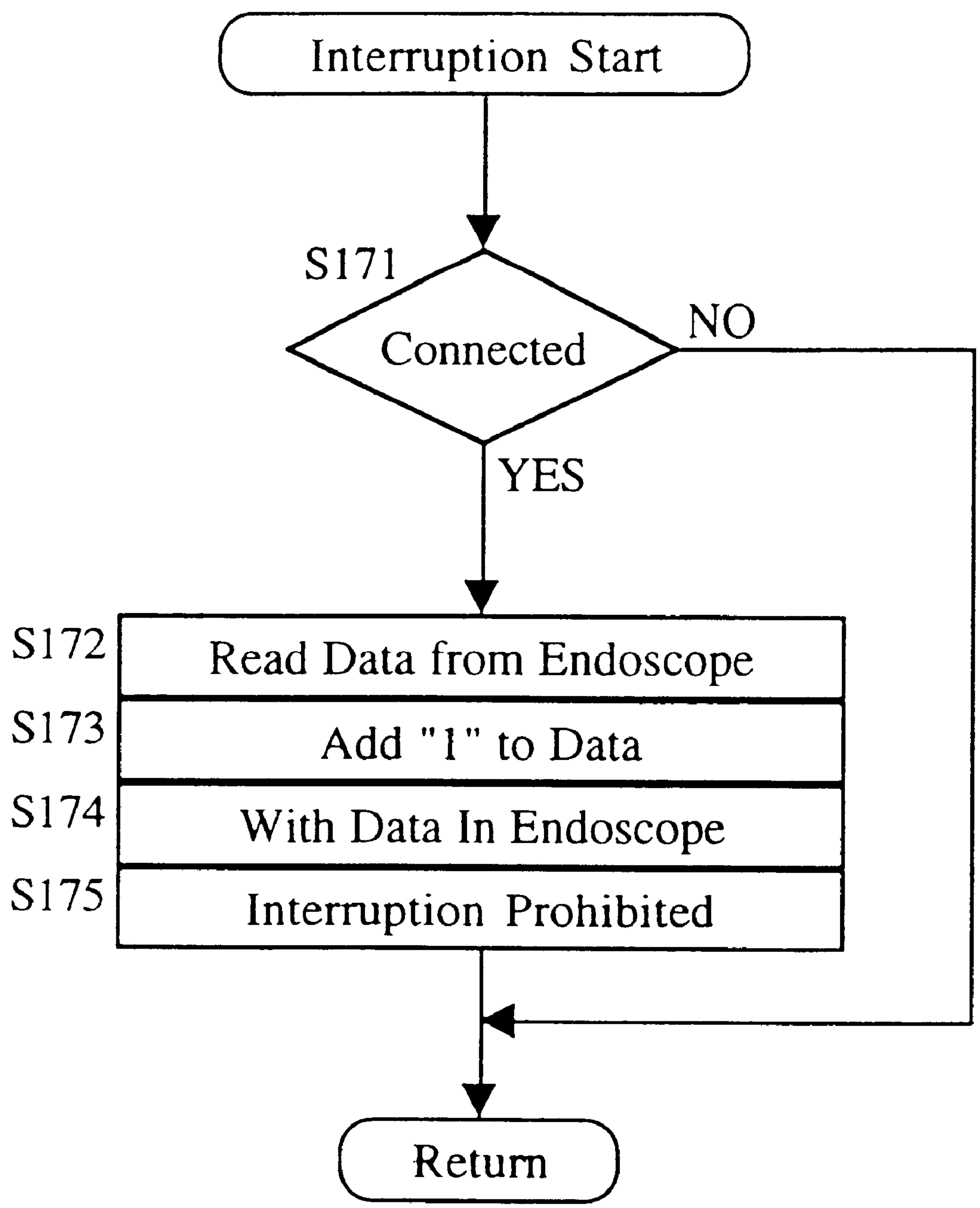
FIG. 21 shows a flow chart of an interruption processing program according to the fourth embodiment; and, FIG. 22 shows a schematic view of the storage area of a RAM according to the fourth embodiment.

The interruption is executed based on the program shown in a flow chart of FIG. 21. For caution's sake as at step S113, whether or not the connector 16 of the endoscope 10 is connected to the video processor and light source device 20 is judged at step S171. This step is executed as a precaution and is therefore negligible.

Subsequently, if the connector 16 is disconnected, the interruption is finished without execution. To the contrary, if the connector 16 of the endoscope 10 is connected to the video processor and light source device 20, the number of connections of the endoscope 10 is read from the storage cell 19 of the endoscope 10 at step S172, and "1" is added to the data at step S173 to write the result in the storage cell 19 of the endoscope 10 at step 174. Finally, for caution's sake, the programmable interruption controller (PIC) 41 is brought to the state that interruption can not be executed at step S 175.

Referring to FIG. 20 again, if the variable u1 is not "1" at step S162, which means it is not just after the initial setting and the connector 16 was connected to the video processor and light source device 20 at the last checking, whether or not the connector 16 is disconnected from the video processor and light source device 20 is checked at step S167 as at step S163.

Then, if the connector 16 is judged to be connected also, the sequence immediately advances to the lamp-related process at step S3. To the contrary, if the connector 16 is disconnected, the variable u1 is set to zero at step S168 and the interruption is prohibited at step S169, then the sequence advances to the lamp related process at step S3.

The present invention is not limited to the above embodiment and a part or all of integration means for number of connections may be mounted on the endoscope side for example. Further, the storage means for storing number of connections may be mounted on the side of essential device such as the video processor and light source device.

With the construction described above, the number of connections of each endoscope in a various types of endoscopes is read at once from the total usage operating time storage means without connecting each endoscope to the essential device one by one, and the data is displayed in a table on the monitor or the like, which permits the number of connections of each endoscope to be confirmed at a glance. The indication on the monitor may be carried out by depressing the F9 key of the keyboard 24.

Figure 22:
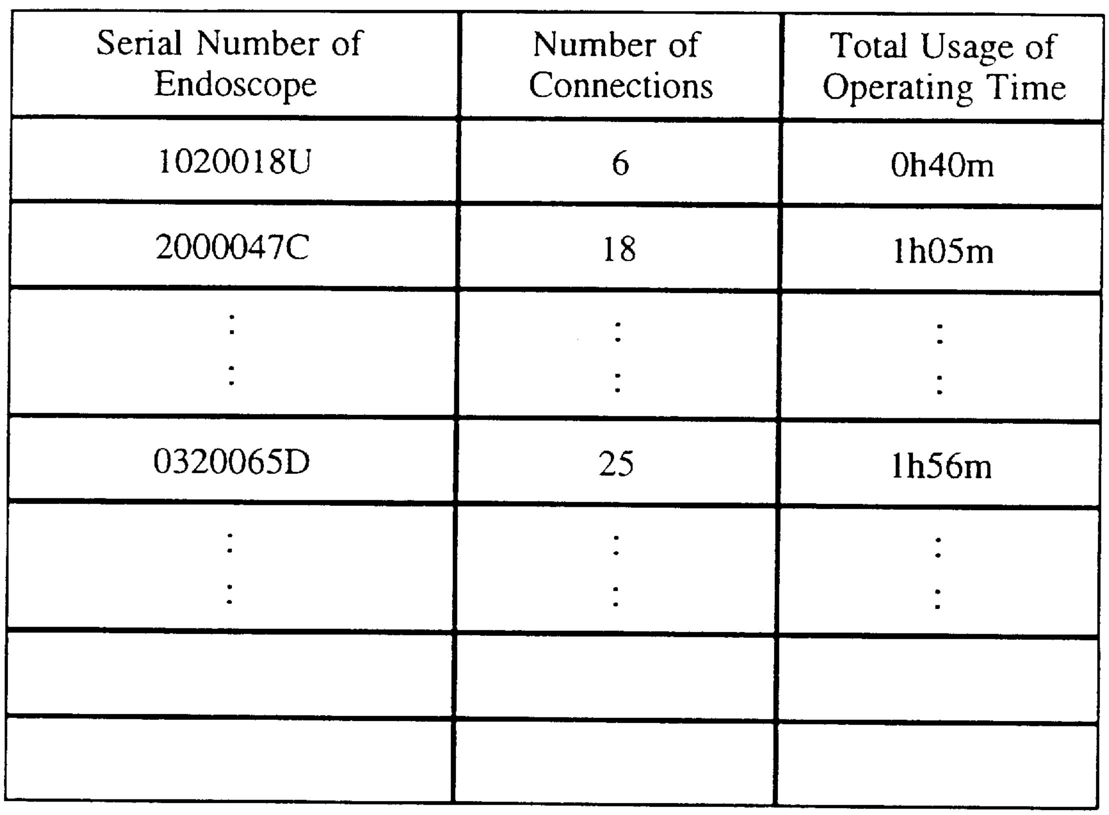

For the above purposes, the storage area of the RAM 34 in the microcomputer 30 should be extended, for example as illustrated in FIG. 22, and area where the number of connections is prepared in accordance with the number of every endoscope. The number of connections of the endoscope 10 is written in the storage area of the RAM 34 at the processing at step S117 in FIG. 16.

In the present invention, the video processor and light source device includes a single light source, a single video processor, or other devices essential to the endoscope. Further, the device essential to the endoscope includes not only a unit such as a light source device and a video processor but also an element or a part composing such unit device.

The present invention is applicable to an endoscope in which image is transmitted through image guide fiber bundle.

With the construction of the endoscopic apparatus according to the present invention, since the number of connections of each endoscope is stored in the storage cell, the number of connections of the endoscope can be displayed, and when the number of connections reaches the standard maintenance value the result is displayed and alarm is actuated, which prevents the overuse of the endoscope in advance. As a result, the failure of the endoscope system or the accidents caused by the system are avoidable through inspection, maintenance and exchange worn parts.

As a result of employing this apparatus the manufacturer of endoscopes will be able to easily gather data on the relationship between the total usage time, the number of operations and types of failures, this will contribute greatly to improvements and quality through the feedback of this data to designers.

In the case where the storage means is mounted on the endoscope side, the number of connections of the endoscope can be checked regardless of the support device to which the endoscope is connected. On the other hand, the storage means is attached on the support device side, the number of connections of many endoscopes is confirmed at a glance with a table without connecting each endoscope one by one. Although the total usage operating time of the endoscope is calculated or the number of connections thereof is counted in the embodiments illustrated in the drawings, both of them may be carried out at the same time by combining those functions of the apparatus.

We claim:

1. An endoscope apparatus comprising:

at least one endoscope;

a peripheral device including a light source;

a detachable connecting device to connect said at least one endoscope and said peripheral device;

means for measuring an emission time or illumination duration of said light source when said endoscope and said peripheral device are connected;

accumulating means, provided in said peripheral device, for accumulating and storing said emission time or illumination duration;

means for indicating said accumulated emission time or illumination duration stored in said accumulation means;

wherein indication by said indicating means is independent of the connection between said at least one endoscope and said peripheral device.

2. The endoscope apparatus according to claim 1, wherein said endoscope apparatus further comprises:

a device for issuing a warning when said accumulated emission time or illumination duration stored in said accumulating means exceeds a predetermined standard time as a result of comparing said accumulated emission time or illumination duration and said predetermined standard time.

3. The endoscope apparatus according to claim 2, wherein said endoscope apparatus further comprises:

means for identifying a type of said endoscope; and means for setting said predetermined standard time in accordance with said type of said endoscope identified by said identifying means.

* * * * *